United States Patent
Rao et al.

(10) Patent No.: US 8,541,197 B2
(45) Date of Patent: Sep. 24, 2013

(54) TARGETS, INCLUDING YAP1, FOR ANTIFUNGAL DRUG DISCOVERY AND THERAPY

(75) Inventors: Reeta Prusty Rao, Newton, MA (US); Samuel Michael Politz, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 428 days.

(21) Appl. No.: 12/517,971

(22) PCT Filed: Dec. 10, 2007

(86) PCT No.: PCT/US2007/086998
§ 371 (c)(1),
(2), (4) Date: Oct. 25, 2010

(87) PCT Pub. No.: WO2008/073900
PCT Pub. Date: Jun. 19, 2008

(65) Prior Publication Data
US 2011/0033442 A1  Feb. 10, 2011

Related U.S. Application Data

(60) Provisional application No. 60/869,231, filed on Dec. 8, 2006.

(51) Int. Cl.
*C12Q 1/18* (2006.01)
*C12Q 1/02* (2006.01)

(52) U.S. Cl.
USPC .............................................. 435/32; 435/29

(58) Field of Classification Search
None
See application file for complete search history.

(56) References Cited

U.S. PATENT DOCUMENTS

| 6,518,035 B1 | 2/2003 | Ashby et al. |
| 2003/0086871 A1 | 5/2003 | Ausubel et al. |

FOREIGN PATENT DOCUMENTS

| WO | WO03/067997 | 8/2003 |

OTHER PUBLICATIONS

Fahlen et al, (Gravit Space Biol Bull. 2005, Abstract only ).*
Jain, C. et al., "A Pathogenic Assay Using *Saccharomyces cerevisiae* and *Caenorhabditis elegans* Reveals Novel Roles for Yeast AP-1, Yap1, and Host Dual Oxidase BLI-3 in Fungal Pathogenesis", Eukaryotic Cell, Aug. 2009, 8 (8):1218-1227.
Joshua, G.W.P. et al., "A *Caenorhabditis elegans* model of *Yersinia* infection: biofilm formation on a biotic surface", Microbiology, 2003, 149:3221-3229.
European Search Report issued Jun. 6, 2010.
Michael G. Smith et al. "Microbial Synergy via an Ethanol-Triggered Pathway." Molecular and Cellular Biology. 2004. 5, vol. 24, No. 9, pp. 3874-3884.
Susan Jones "Social Drinking." Nature Reviews Microbiology. 2004. 6, vol. 2, p. 445.

* cited by examiner

*Primary Examiner* — Padma V Baskar
(74) *Attorney, Agent, or Firm* — Duane Morris LLP (57) ABSTRACT

The present invention is based on the discovery of a two organism model system that can be used to identify virulence factors. The system is also useful in the process of drug delivery. More specifically, we have established valid fungal infection in *caenorhabditis elegans* with an invading pathogen, the yeast *Saccharomyces cerevisiae*. Because both species are genetic model organisms, the assay can be used to identify host and virulence factors involved in such interactions.

3 Claims, 4 Drawing Sheets

| Strain | day4 | day5 |
|---|---|---|
| E.coli | 0 | 0 |
| yeast heat killed | 0 | 0 |
| yeast WT | 63% | 5% |
| yap1 | 0 | 0 |
| yap2 | 0 | 0 |
| yap3 | 0 | 0 |
| yap4 | 41% | 0% |
| yap5 | 0% | 0% |
| yap6 | 0% | 0% |
| yap7 | 0% | 0% |
| sod1 | 0 | 1% |

Figures 6A and 6B

TARGETS, INCLUDING YAP1, FOR ANTIFUNGAL DRUG DISCOVERY AND THERAPY

CROSS-REFERENCE TO RELATED APPLICATIONS

This application is a U.S. National Stage Application of International Application No. PCT/US2007/086998, filed on Dec. 10, 2007, which claims the benefit of the filing date of U.S. Application No. 60/869,231, which was filed Dec. 8, 2006. The contents of each of these prior applications are hereby incorporated by reference in their entirety.

TECHNICAL FIELD

This invention relates to compositions and methods that can be used to identify antifungal agents, and more particularly to two-organism model systems for identifying host and virulence factors.

BACKGROUND

Currently, fungal infections are treated with agents such as amphotericin B, 5-flucytosine, caspofungin, or various azole derivatives (e.g., fluconazole, ketoconazole, and itraconazole). None of these agents are effective on all fungal infections, and all of the known therapies carry with them some level of human toxicity. Increasing levels of resistance to known therapies also presents a problem. Despite efforts to minimize toxicity and maximize potency of the azoles since the 1970s, amphotericin B, a drug introduced in the 1950s, remains the best choice for many serious mycoses, and, in particular, disseminated mycoses. This remains the case despite the drug's significant toxicity and problems with resistance and non-availability of an absorbable oral form for long-term maintenance. Attempts to encapsulate amphotericin B into liposome vesicles to diminish toxicity have proven only moderately successful.

SUMMARY

The present invention is based, in part, on our discovery of a two-organism model system that can be used to identify virulence factors. The system is also useful in the process of drug discovery (i.e., in discovering anti-fungal agents). More specifically, we have established valid fungal infection in *Caenorhabditis elegans* (*C. elegans*) with an invading pathogen, the yeast *Saccharomyces cerevisiae* (*S. cerevisiae*). Because both species are genetic model organisms, the assay can be used to identify host and virulence factors involved in such interactions. Accordingly, the invention features co-cultures of these organisms, including co-cultures in which one or the other is mutant (e.g., a wild type *C. elegans* is co-cultured with a mutant fungi (e.g., *S. cerevisiae*) or vice versa). For a control experiment or for generating data that can be used as a reference standard, the co-culture can include a wild type *C. elegans* and a wild type fungal pathogen (e.g., a wild type *S. cerevisiae*). The co-culture can be, or can be a part of, a model system, and the fungal pathogen (e.g., *S. cerevisiae*) can have a mutation that renders the fungal pathogen (e.g., the *S. cerevisiae*) less able to infect the *C. elegans*. This indicates that the wild type correlate of the mutant gene encodes a protein that facilitates infection. That protein and the gene that encodes it are therefore targets for pharmaceutical intervention and can be used in assays to identify antifungal agents. Agents, such as small molecules, antibodies, other proteins, or nucleic acids that inhibit the wild type correlate are candidate anti-fungal agents. The mutant *S. cerevisiae* can be one that comprises a mutation in a gene that is expressed in *S. cerevisiae* but not in a mammal.

Where the co-culture and/or model system includes a mutant *C. elegans*, the mutation can be one that renders the *C. elegans* either more or less susceptible to infection by a wild type *S. cerevisiae*. Where the mutant *C. elegans* is more susceptible to infection than a wild type *C. elegans*, the wild type correlate of the mutant gene must normally protect the *C. elegans* from infection. Agents that mimic the wild type correlate in higher animals (e.g., in mammals, including humans) are therefore candidate antifungal agents. Where the mutant *C. elegans* is less susceptible to infection, the mutation must be of a gene that, in its wild type form, permits or facilitates infection. Therefore, targeting the gene in the host so that it fails to be expressed, fails to function as it naturally would, or fails to permit or facilitate fungal infection, possibly while otherwise functioning normally, would render a host less susceptible to infection and/or provide a means for treating infection. The methods of the invention can include the step of identifying the protein that is mutant in *C. elegans* and the homolog of that protein in a higher animal (e.g., a mammal, including a human). The protein that is mutant in *C. elegans* can be a protein that, in its wild type form, would permit or facilitate infection. The methods can further include the step of identifying an agent that acts as an antifungal agent by virtue of the agent's ability to inhibit an activity of the wild type protein in a host (e.g., a mammal, including a human). For example, the agent may act as an antifungal agent by inhibiting the target protein's role in infection.

Any of the co-cultures and any of the model systems can include a *C. elegans* and a fungal pathogen that are co-cultured on a solid medium. In some instances (e.g., where numerous pairs of organisms are being screened), it may be preferable to construct the system in a liquid medium.

In another aspect, the invention features methods of identifying a virulence factor relevant to fungal pathogenesis. The methods can include the steps of: (a) providing a co-culture comprising a *C. elegans* and a fungal pathogen comprising a mutant gene; and (b) determining whether the fungal pathogen infects the *C. elegans*, wherein a lack of infection identifies the protein encoded by the wild type correlate of the mutant gene as a virulence factor. In these methods, the fungal pathogen can be *S. cerevisiae* and can have, or can include, a mutation in a gene that is expressed in the fungal pathogen but not in a mammal.

In another aspect, the invention features a virulence factor identified by the methods described herein. The methods of identifying a virulence factor may result in the identification of an enzyme or transcription factor (e.g., a transcription factor in the yap family).

In another aspect, the invention features methods of identifying an antifungal compound. The methods can include the steps of: (a) providing a co-culture comprising a *C. elegans* and a fungal pathogen comprising a mutant gene; (b) determining whether the fungal pathogen infects the *C. elegans*, wherein a lack of infection identifies the protein encoded by the wild type correlate of the mutant gene as a virulence factor; (c) exposing a wild type fungal pathogen that expresses the virulence factor to a test compound; and (d) determining whether the test compound inhibits expression of the virulence factor, wherein a decrease in the expression of the virulence factor indicates that the test compound is an antifungal compound. In a subsequent step, one can administer the antifungal compound to a mammal (e.g., a human) and determine whether the compound inhibits fungal infection in the mammal (e.g., by reducing one or more of the signs or symptoms associated with the fungal infection). In any of the methods of identifying an antifungal compound, the fungal pathogen can be *S. cerevisiae* and the fungal pathogen can have, or can include, a mutation in a gene that is expressed in the fungal pathogen but not in a mammal. The compound can be any type of agent, including a small organic or inorganic molecule, an antibody or other protein, or a nucleic acid.

In another aspect, the invention features an anti-fungal compound identified by the methods described herein.

The *S. cerevisiae*-based assay described herein can be used to study the genetic and molecular mechanisms of fungal virulence. This model system can be used not only for the identification of fungal genes important for mammalian pathogenesis, but also for identification of alternative target pathways for antifungal drug development and continued exploration of host innate immune responses to fungal infections.

In another aspect, the invention features methods of treating a patient who has, or who is at risk of developing, a fungal infection. The methods can include the steps of: (a) providing a co-culture comprising a *C. elegans* and a fungal pathogen comprising a mutant gene; (b) determining whether the fungal pathogen infects the *C. elegans*, wherein a lack of infection identifies the protein encoded by the wild type correlate of the mutant gene as a virulence factor; (c) exposing a wild type fungal pathogen that expresses the virulence factor to a test compound; (d) determining whether the test compound inhibits expression of the virulence factor, wherein a decrease in the expression of the virulence factor indicates that the test compound is an antifungal compound; and (e) administering an effective amount of the antifungal compound to the patient.

In another aspect, the invention features methods of identifying a host factor that promotes fungal pathogenesis. The methods can include the steps of: (a) providing a co-culture comprising a *C. elegans* includes one or more mutant genes and a wild type fungal pathogen; and (b) determining whether the fungal pathogen infects the *C. elegans*. A lack of infection identifies the protein encoded by the wild type correlate of the mutant gene as a host factor that promotes fungal pathogenesis. Infection may be assessed relative to one or more of the events that occur when a fungal pathogen infects a wild type host, and the host factor can be cell surface or membrane-bound protein. More specifically, the host factor can be a receptor for an antigen expressed by the pathogen.

The details of one or more embodiments of the invention are set forth in the accompanying drawings and the description below. Other features, objects, and advantages of the invention will be apparent from the description and drawings, and from the claims.

DETAILED DESCRIPTION

The goal of the studies described below was to develop an assay in which to study host-pathogen interactions for a fungal pathogen, and that assay, the multi-organism model, host factors, virulence factors, and assays for molecules that target them are all aspects of the present invention. We used the nematode *C. elegans* as the model host and *S. cerevisiae* as the invading pathogen. Our studies provide opportunities to identify both host and virulence factors and agents (e.g., small organic molecules and antibodies) that target those factors and thereby influence the host's susceptibility to infection and the pathogen's virulence, respectively. The assay is useful in screening both *C. elegans* and *S. cerevisiae* mutants.

Pathogenesis is the mechanism by which foreign organisms cause disease, and the result can be inflammation, fever, sepsis, and ultimately even death. Our pathogenesis model requires at least two organisms, at least one of which is a host and at least one of which is a pathogen, which are maintained under conditions that permit their interaction (e.g., a coculture where the pathogen can infect the host). As noted, we have chosen to use the well studied genetic model organisms *C. elegans* and *S. cerevisiae*. For the present assays, co-cultures of these organisms can be configured for high throughput studies (e.g., in multi-well plates (e.g., 96-well plates)) in which potential antifungal agents are applied singly or in small groups to parallel cultures. Where a desired effect is observed (e.g., where an agent inhibits the pathogen or improves the host's resistance), the potential agent can be identified and tested further (e.g., in a vertebrate model system).

Agents useful as anti-fungal agents can be identified from libraries (e.g., combinatorial or compound libraries, including those that contain synthetic and/or natural products, and custom analog libraries, which may contain compounds based on a common scaffold). Such libraries can include hundreds or thousands of distinct compounds or random pools thereof. Libraries suitable for screening can be obtained from a variety of sources, including the compound libraries from ChemBridge Corp. (San Diego, Calif.). Another compound library is available from the consortium formed by the University of Kentucky, the University of Cincinnati Genome Research Institute and the Research Institute of the Children's Hospital of Cincinnati. The library is referred to as the UC/GRI Compound Library. The compound libraries employed in this invention may be prepared by methods known in the art. For example, one can prepare and screen compounds that target host or virulence factors (e.g. Yap1) by any means including, but not limited to, combinatorial chemistry techniques, fermentation methods, plant and cellular extraction procedures and the like. Methods for making combinatorial libraries are well-known in the art. See, for example, E. R. Felder (*Chimia* 48:512-541, 1994); Gallop et al. (*J. Med. Chem.* 37:1233-1251, 1994); R. A. Houghten (*Trends Genet.* 9:235-239, 1993); Houghten et al. (*Nature* 354:84-86, 1991); Lam et al. (*Nature* 354:82-84, 1991); Carell et al. (*Chem. Biol.* 3:171-183, 1995); Madden et al. (Perspectives in Drug Discovery and Design 2, 269-282); Cwirla et al. (*Biochemistry* 87:6378-6382, 1990); Brenner et al. (*Proc. Natl. Acad. Sci. USA* 89:5381-5383, 1992); Gordon et al., (*J. Med. Chem.* 37:1385-1401, 1994); Lebl et al. (*Biopolymers* 37:177-198, 1995); and references cited therein.

There are two types of immunity, innate and adaptive. An important host factor in pathogenesis is failure of the adaptive immune response, which leaves the organism with only an innate immune response to overcome the infection. Facets of the host defense mechanisms, including innate immunity, are evolutionarily conserved from nematodes to mammals. In many cases, microbial genes essential for virulence in mammalian models have been shown to be required for maximum pathogenicity in nematodes. These studies have primarily explored bacterial species and have tested few fungal species (for recent review see (6)).

Innate immunity functions as a rapid response to infection. Antigen receptors in innate immunity are of limited diversity and specificity. This simple form of immunity is common to all animals. Molecular studies of the pathways and components of innate immunity indicate that they are conserved between invertebrates and vertebrates. This innate immunity can be studied in simple invertebrate model organism.

Adaptive immunity is only present in vertebrate animals and is more specific than innate immunity, exhibiting unlimited antigenic specificity, diversity in antibodies and other receptors, and presence of memory cells. However adaptive immune responses are relatively slow.

C. elegans is a non-parasitic soil-living nematode that has innate immune responses that defend it against pathogens (Ausubel and Kim, 2005). C. elegans docs not have adaptive immunity. The nematode's first means of defense is its cuticle. The cuticle forms a physical barrier an invading pathogen encounters. It has been observed that due to the properties of the cuticle, only a few bacterial and fungal pathogens have the ability to attach or decompose the extracellular exoskeleton of the worm (Gravato-Nobre and Hodgkin, *Cell. Microbiol.* 7:741-751, 2005).

Two categories of virulence factors are produced by microbial pathogens that infect *C. elegans*: toxin-mediated and infection-mediated. These two virulence mechanisms can be slow or fast killing, but not all pathogens evoke an immune response. Toxin-mediated interactions may produce factors that can indirectly cause an immune response whereas infection-mediated interactions require direct contact between the pathogen and host. The cuticle of *C. elegans* is composed of five layers, containing lipids, glycoproteins and collagen. It has three openings, which are potential sites for infection. Interactions can be external, by adhesion to the cuticle, or internal by ingestion. A factor involved in these two virulence mechanisms is the amount of the pathogen that is required to induce an immune response in the host (Alegado et al., *Cell. Microbiol.* 5:435-444, 2003; Kim and Ausubel, *Curr. Opin. Immunol.* 17:4-10, 2005).

Model organisms are a useful tool in the world of biological studies. They are used for their similarity to higher organisms such as humans. Nematodes are typical animals in terms of their genetics, cell biology, developmental biology, neurology, endocrinology, toxicology, and immunology (Zuckerman, 1980). Model organisms are simpler and less complex than humans, which aids understanding of basic principles which can then be applied to understanding of higher, more complex organisms. The two organisms used in our project, *Caenorhabditis elegans* and *Saccharomyces cerevisiae*, are important because both genomes are completely sequenced and mutants are readily available. *C. elegans* make a good model for our study because these animals have genes with vertebrate homologs. The worms hermaphroditic nature and lifespan of two weeks allows for extensive observation (Alegado et al., supra). *S. cerevisiae* is important in this study because it undergoes a dimorphic transition in which it can grow as a budding form or a filamentous form. This is a characteristic that is shared by other pathogenic fungi. Homologs of genes and pathways identified in *S. cerevisiae* have been shown to be important in true fungal pathogenesis. *S. cerevisiae* is also important because a library of gene targeted deletion mutants is available.

Using two model organisms within one study plays a key role in the context of a genetic screen. This is of great importance because it allows for identification of specific genes involved in both sides of the equation in host-pathogen interactions. This can then in turn be related to other infections.

Previous Pathogenesis Studies: Host-pathogen interactions have been studied using *C. elegans* in previous studies with bacterial pathogens. Relevant bacterial infections of *C. elegans* are those caused by *Microbacterium nematophilum* and *Y. pseudotuberculosis* which infect wild type *C. elegans*. Some surface (srf) mutants show resistance to these infections. The biofilm formed by *Y. pseudotuberculosis* and the anal infection by *M. nematophilum*, do not occur in the surface (srf) mutants. This is because surface (srf) mutants have alterations in cuticle structure and composition. The bacterial unswollen (bus) mutants as well as the bacterial adhesion (bah) mutants also show resistance to the biofilm infection caused by *Y. pseudotuberculosis*. These studies have shown the role of the cuticle in microbial infections of *C. elegans* (Nicholas and Hodgkin, 2004; Gravato-Nobre et. al., supra).

Figure 1:
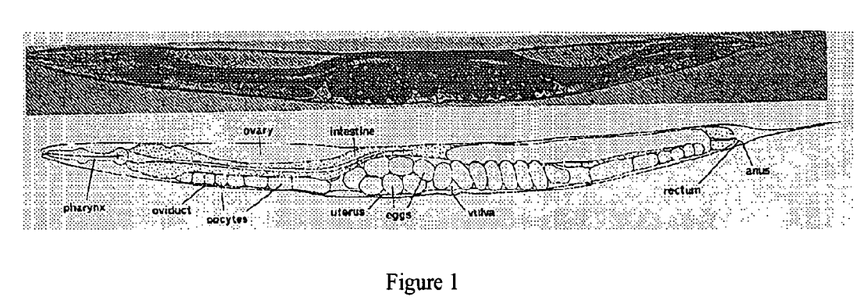
FIG. 1 is a sketch of *C. elegans* adult hermaphrodite (Wood et al., 1988).

*C. elegans* have an innate immune system, but lack an adaptive immune system (Alegado et al., supra). In innate immunity, external and physiological barriers and a rapid inflammation response protect an organism from infection. Organisms without an adaptive immune system have only their innate immune mechanisms in which to protect themselves from pathogens. This innate immunity response is a primary and rapid response (Gravato-Nobre and Hodgkin, supra). Within the innate immune system there is the mechanism of a physical barrier. The nematodes' first means of defense is the cuticle. The cuticle is composed of five layers: the surface coat, the epicuticle layer, the cortical, and the medial and basal layers. The surface coat or glycocalyx is composed of lipids and glycoproteins. Composition of the epicuticle is unknown; the inner three layers are composed of collagen (Wood, *The Nematode Caenorhabditis elegans*, Cold Spring Harbor Laboratory, Cold Spring Harbor, N.Y., 1988). The cuticle has openings at the mouth, vulva and anus. These openings allow for possible infection. A known response to infection is tail swelling at the site of a rectal infection due to colonization of the pathogen, *M. nematophilum*. This innate immune response of tail swelling also causes mild constipation reducing the possibility of severe constipation or death (Nicholas and Hodgkin, 2004). Another form of protection is the worm's pharyngeal grinder, which "is made up of three pairs of simultaneously contracting muscle cells, which break open bacteria [or yeast] as they pass back to the intestines" (Alegado et al., supra, pg. 441). This tract goes from the esophagus to the pharynx to the intestines and finally to the anus, where the worms' last defense is the mechanism of defecation. Bacteria or yeast that remains undamaged through the process of eating will be discharged. FIG. 1 shows a sketch of an adult hermaphrodite *C. elegans*.

Aside from the physical barriers of the innate immune, *C. elegans* has the ability to avoid detected pathogens by chemotaxis (see Gravato-Nobre and Hodgkin, supra). If a microbe is toxic to the worm it has the ability to avoid it and therefore not eat the provided food source.

*S. cerevisiae* has proven to be a good model for fungal pathogenesis. It has the ability to switch from a yeast form to a pseudohyphal or filamentous form. Pseudohyphae are chains of cells created by the failure of separation between the mother and daughter cell during division, despite visible signs of division. Hyphae are elongated filaments that do not show signs of separation. Different cell surface proteins are required in this transition. Nonfilamentous mutants of yeast have been shown to be avirulent (Lo, Cell 90:939-949, 1997), showing that the filamentous form of yeast plays a role in the invasion of a host. Once the filamentous yeast has invaded the host, the filamentous form may increase the interactions between the pathogen and host. For example, the MAP kinase pathway involved in the filamentation response in yeast has proved to be important in true pathogenic fungi, such as *U. maydis* (plant pathogen) and *C. albicans* (human pathogen). Genes that are responsible for filament formation encode proteins required by virulence factors which are important to pathogenesis (Liu, 2001).

*C. elegans* is used as a model organism in scientific studies. It is a useful organism in which to study genetics, immunity and various other disciplines. In the natural world it is a soil inhabitant and is exposed to a variety of bacteria and other potential pathogens. Its genome (100 Mb) has been completely sequenced. Wild-type (N2) and mutant strains are readily available for research. Its predominant sex is hermaphrodites with the occasional male. The worms' transparent nature allows for good observational conditions. *C. elegans* food source in the laboratory is *Escherichia coli*. Worms eat by means of muscular pumping and peristalsis in the pharynx, which breaks up particles of ingested bacteria. The terminal bulb of the pharynx contains the grinder, which breaks up the particles. When the terminal bulb relaxes bacteria remains in the lumen of the corpus while liquid is removed; after approximately four pumping motions a peristalsis wave moves the particles to the intestines (Wood, 1988).

Figure 2:
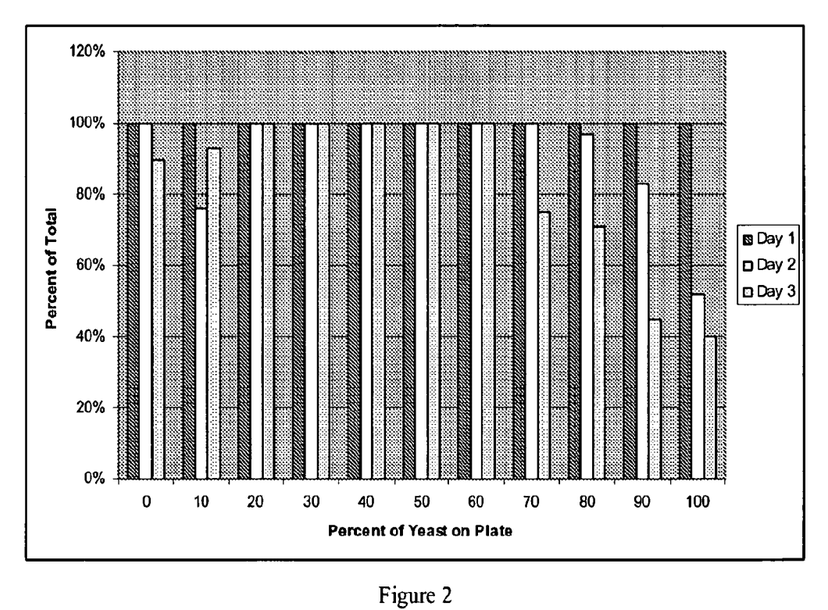
FIG. 2 is a bar graph of 10% interval test count over three days.

The nematodes' generation time is about three days, starting from the hatched egg and progressing with molts at each larval stage (L1, L2, L3 and L4). During the molts, a new cuticle is made and the old one is shed. After the final molt, *C. elegans* becomes a fertile adult, approximately 1 mm long, for about four days and then lives on for about another ten days. After fertilization, the egg creates a tough shell for protection, then about three hours after fertilization the egg is laid. The next step in development is embryogenesis which is the combination of cell proliferation and morphogenesis. During the cell proliferation phase the cells divide and locate to their specific spatial patterns within the egg. During morphogenesis, after which there are about 550 cells, the larvae body lengthens, neural pathways are completed, and the cuticle is synthesized. At 25° C., fourteen hours after fertilization the L1 larvae hatches from the egg. The L1 hermaphrodite consists of 558 somatic cells and is 250 µm long. Within the following fifty hours the next three larval stages continue with further development of the cuticle, nervous system, muscular system and reproductive structures. During molting the grinder ceases pumping actions temporarily; this process is called lethargus. Gonadogenesis is finalized at the L4 larval stage. At the L3 and L4 larval stages no fertilized eggs are present within the uterus of the worm. The L3/L4 stage worms can be identified by a white patch where their vulva will develop; they are also significantly smaller in size then adult worms. At the adult stage the vulva is fully developed, oocytes are formed and self-fertilization can now occur. Each unmated hermaphrodite lays approximately 300 self-fertilized eggs, but a mated hermaphrodite can produce up to 1000 progeny. FIG. 2 shows a diagram summarizing the development of *C. elegans* as well as the approximate time scheme. The numerical values on the outside of the circle represent hours after fertilization and the values inside the circle represent hours after the L1 hatches (Wood, pg. 1988).

EXAMPLES

Example 1

*Caenorhabditis elegans* Mutants:

The *C. elegans* mutants used in this pathogenesis study were bacterial unswollen mutants (bus), surface mutants (srf) and bacterial adhesion mutants (bah). Bacterial unswollen mutants are resistant to *M. nematophilum*. Bacterial adhesion mutants are resistant to *Y. pseudotuberculosis* and surface mutants are resistant to both. These resistant mutants do not show the evidence for colonization at the site of infection, i.e., the tail swelling characteristic of *M. nematophilum* or the biofilm produced on the *C. elegans* head by *Y. pseudotuberculosis*.

*Saccharomyces cerevisiae*:

The yeast *S. cerevisiae* is a model organism whose genome is also completely sequenced and used in scientific studies. It has been shown to act as a pathogen in plants, but has not been studied as a pathogen in *C. elegans*. This particular yeast is widely studied and an extensive single gene-targeted deletion library has been created. The availability of this library is an important reason why *S. cerevisiae* was chosen for this study. Also, no other fungi are amenable to genetic manipulation. We will be using, RPY101, the parent strain for this library, to develop the assay.

*S. cerevisiae* Mutants:

The *S. cerevisiae* mutants used in this pathogenesis study were the series of flocculation mutants. The flocculation genes are: FLO1 (RPY695 and RPY699), FLO5 (RPY693), FLO9 (RPY694 and RPY700), FLO10 (RPY696), and FLO11 (RPY5953). Flocculation is cell to cell adhesion, due to adhesins (also called flocculins) which are cell surface proteins that can adapt with the environment which they are in. The flocculation response of FLO11 is important to fungal pathogenesis, allowing cells to adhere to the host or an infection area. Yeast cells have the ability to identify an infection site, and then will adhere to the host, colonizing the area and invading the host or creating a biofilm. The adaptation property of adhesins allows for a wide range of infection possibilities (Verstrepen, 2006). As a result of these cell surface interactions, yeast cells form what are called "flocs" in which numerous cells adhere to one another. FLO1, FLO5, FLO9, and FLO10 flocculation genes exhibit cell to cell adhesion, whereas FLO11 mutants exhibit adhesion to substrates (such as agar). FLO1 shows strong flocculation and FLO10 shows weak flocculation.

There are two types of adhesion mechanisms: lectin-like adhesion (sugar sensitive) and sugar-insensitive adhesion. FLO1, FLO5, FLO9, and FLO10 have cell surface interactions by lectin-like adhesion. FLO11's mechanism is that of sugar-insensitive adhesion. Under stress conditions, FLO11 is activated and promotes the yeast cells to adhere to substrates, foraging for nutrients. The flocculation then allows cells in the middle of the flocs protection from a stressful environment. The involvement of the Flo genes in surface adhesion promoted us to use these mutants.

The approach to this study was to co-culture *S. cerevisiae* and *E. coli* with *C. elegans* and observe changes in *C. elegans* phenotypes indicative of yeast infection. Likely candidates for altered host-pathogen interactions were tested by including *C. elegans* or *S. cerevisiae* mutants in the co-culture assay.

*C. elegans* Stocks:

Worms were maintained on 60 mm diameter NG Agar stock plates (Brenner, *Genetics* 77:73, 1974) supplied with *E. coli* OP50 lawns. The lawn was made from an overnight liquid culture of *E. coli* (OP50) in Hershey Broth (see the description below for the composition of this and other components useful in the present assays) and served as a food source for the worms. For stock maintenance, three worms were picked off an existing plate and placed on a new plate, every three to four days. Plate cultures were incubated at 20° C. The wild-type Bristol variety N2 strain of C. elegans was used to study the pathogenesis assay.

The particular strains used were as follows: BR2408 srf-3 (e2789) unc-30 (e91) and BR2435 srf-3 (e2689), DC6 srf-3 (br6), DC3 srf-2 (br3), DC2 bus-17 (br2), DC4 bus-4 (br4), DC9 bah-3 (br9), DC8 bah-2 (br8), and DC1 bah-1 (br1). A genotype table is shown below in Table 1 for the wild type strain and mutant strains.

TABLE 1

C. elegans Genotypes

| Strain | Genotype | Mutation |
|---|---|---|
| N2 | Wild type | |
| BR2408 | srf-3 (e2789) unc-30 (e91) | Stop after aa88 |
| BR2435 | srf-3 (e2689) | Stop after aa60 |
| DC4 | bus-4 (br4), | |
| DC2 | bus-17 (br2) | |
| DC1 | bah-1 (br1) | |
| DC8 | bah-2 (br8) | |
| DC9 | bah-3 (br9) | |
| DC6 | srf-3 (br6) | 110 base pair deletion |
| DC3 | srf-2 (br3) | |
| AT18 | srf-6 (yj13) | |

S. cerevisiae Stocks:

Yeast strains were maintained on YPD Agar (Guthrie and Fink, *Methods in Enzymology* 194, 1991) plates for storage. Yeast strains were streaked onto a new plate every three weeks, and stored at 4° C. when not in use. The yeast strain used for assay development was the haploid RPY101. The flocculation genes tested were as follows: FLO1 (RPY695 and RPY699), FLO5 (RPY693), FLO9 (RPY694 and RPY700), FLO10 (RPY696), and FLO11 RPY5953). Table 2 shows a genotype table for *S. cerevisiae*, including the parent strain and mutant types.

TABLE 2

S. cerevisiae Genotypes

| Strain | Genotype |
|---|---|
| RPY101 | MATa his3Δ1 leu2Δ0 met15Δ0 ura3Δ0 |
| RPY693 | flo5Δ MATa his3Δ1 leu2Δ0 met15Δ0 ura3Δ0 |
| RPY694 | flo9Δ MATa his3Δ1 leu2Δ0 met15Δ0 ura3Δ0 |
| RPY695 | flo1Δ MATa his3Δ1 leu2Δ0 met15Δ0 ura3Δ0 |
| RPY 696 | flo10Δ MATa his3Δ1 leu2Δ0 met15Δ0 ura3Δ0 |
| RPY699 | flo1Δ MATa his3Δ1 leu2Δ0 met15Δ0 ura3Δ0 |
| RPY700 | flo9Δ MATa his3Δ1 leu2Δ0 met15Δ0 ura3Δ0 |
| 5953 | flo11Δ MATa his3Δ1 leu2Δ0 met15Δ0 ura3Δ0 |

Maintenance of E. coli and S. cerevisiae Cultures:

To spot plates for experiments, liquid cultures of yeast and E. coli OP50 were grown. Yeast cultures were grown in YPD broth and E. coli cultures were grown in LB broth (see the description in the five-day scheme below); yeast cultures were shaken overnight at 30° C. and E. coli cultures were shaken overnight at 37° C. One colony of bacteria or yeast was inoculated in a 5 mL liquid culture. Cultures were made fresh for each experiment.

Preparation of Experimental Plates:

Experimental plates were 35 mm in diameter and contained 2 mL of NG Agar. Some plates contained 200 μg/mL Ampicillin and 15 μg/mL Gentamicin. Antibiotics were added to the NG agar after autoclaving and cooling the solution. Antibiotics were used for plates spotted with yeast so that E. coli transferred with worms from the stock plate would not grow to create an unwanted food source for the worms. The plates were left at room temperature overnight to solidify. The following day they were spotted with 20 μL of an overnight stationary phase culture of yeast on antibiotic plates or 20 μL of E. coli on non-antibiotic plates. Some plates were spotted with 20 μL of a mixture of yeast and E. coli. The spots were then left to dry at least overnight before the worms were transferred. Plates were stored at 20° C. in an air-tight container.

Egg Preparation:

C. elegans eggs for starting assay cultures were prepared by bleach treatment. Eggs prepared in this way did not introduce E. coli to assay plates, and facilitated large scale study. For egg preparations four 60 mm stock plates of worms were used, which had grown up four to five days at 20° C. prior to doing the experiment. Worms were harvested when the E. coli spot was almost completely consumed and large numbers of eggs were visible under a microscope. Eggs were washed off plates four times with M9 buffer (Brenner, *Genetics* 77:73, 1974), squirting the liquid repeatedly on the agar surface to remove all eggs from the surface of the plate. The washes were collected in a 15 mL polypropylene conical tube. Eggs and worms were centrifuged at 900×g (2000 rpm) for two minutes in a table-top centrifuge. The supernatant was aspirated and fresh M9 buffer was used to resuspend the worms and eggs. After a second similar wash, the supernatant was aspirated and a bleach solution was added to the tube to lyse worms and release eggs. The bleach solution contained 0.25 M NaOH dissolved in a 1:4 (V:V) dilution of commercial bleach in water. The eggs were kept in the bleach solution for five minutes. For the first three minutes the tube was gently inverted to mix the eggs, worms, and bleach, then for the last two minutes the solution was centrifuged at 2000×g (3000 rpm). After centrifugation finished, the bleach solution was removed immediately by aspiration to minimize further exposure of eggs to bleach. The pellet was resuspended in M9 buffer and centrifuged at 2000×g (3000 rpm). After two more similar washes, the egg pellet from the last centrifugation was resuspended in 2 mL of M9 buffer. The eggs were then ready to be put on experimental plates. The number of eggs present was measured by counting eggs in a 5 μL aliquot spotted on to a NG agar plate. If the eggs were too highly concentrated, the solution was diluted with M9 buffer. If the number of eggs was too low, the egg suspension was recentrifuged and the pellet resuspended in a smaller volume. Approximately 30 eggs were dispensed in 5 μL (5-6 eggs/μL) of buffer to the surface of each experimental plate.

Preparation of Fluorescein Isothiocyanate (FITC) Labeled S. cerevisiae:

FITC was dissolved in Dimethyl Sulfoxide (DMSO) at a concentration of 1 mg/ml. The concentration of yeast culture was estimated by measuring absorbance at 600 nanometers in a spectrophotometer, using the conversion factor that an absorbance of 1.0 corresponds to a concentration of $2 \times 10^7$ cells per mL. To concentrate the cells, 2 mL of yeast culture was centrifuged at 15,000×g and the supernatant was discarded after each spin. Next, the cells were washed with 1 mL of Phosphate Buffered Saline (PBS), and resuspended in 1 mL of PBS. To the cell suspension in PBS, 10 μL of the FITC/DMSO solution was added. This mixture was left to incubate for one hour at room temperature. After the incubation period, the cells were washed three times in 1 mL of PBS, pelleting the cells between washes by centrifugation in a microcentrifuge for five minutes. The FITC labeled cells were kept wrapped in aluminum foil to minimize exposure to light and stored at 4° C. Cells were used for up to five days after staining with FITC.

Microscopy of FITC Labeled Yeast Ingested by *C. elegans*:

Blank experimental NG agar plates were spotted with 10 μL of FITC labeled yeast suspension. Worms were added and the plate was incubated at 20° C. for one hour to allow worms to ingest the yeast. To view the worms under the microscope, a 2% agarose pad slide on a microscope slide was prepared containing 0.01 M sodium azide as anesthetic. A 3 μL drop of M9 buffer was added to the solidified agarose pad to create a moist area for mounting worms. Adult worms or larval stage worms were picked from stock plates on the M9 drop on the slide. Different stages of worms were examined on separate slides. Mounted worms were covered with a cover slip. The worms were viewed under a 40× objection and photographs were taken under FITC epifluorescence, DIC, and transillumination optics.

L1 Arrest of *C. Elegans* Grown on *S. cerevisiae*:

An experiment was designed to show what would happen if worms were provided with *S. cerevisiae* as a food source. The test was done in duplicate with two plates spotted with yeast strain RPY101 and two spotted with *E. coli*. To each plate twenty adult worms were added; the plates were incubated at 20° C. and observed after three, six, twenty-four, thirty, and thirty-five hours.

It was observed that the worms on the yeast plates moved slower, laid fewer eggs, and spent less time in the yeast than worms on the *E. coli* plates. The intestinal lumens of worms grown on yeast appeared wider than the lumens of worms that were grown on *E. coli* plates. In addition, yeast-like particles could be seen in the intestinal lumens of the worms. At the end of the experiment, the offspring of the worms placed on the yeast plate appeared much smaller than the offspring of the worms on the *E. coli* plate. Compared to adult sized worm, the size of the offspring on the yeast plate seemed to be that of a first stage larva.

L2 and Further Developed *C. elegans* can Eat *S. cerevisiae*:

Because the offspring that appeared arrested at the L1 stage grew from hatching on the yeast plate, it was important to determine whether the worms actually ate the yeast. The apparent arrest could have resulted from starvation if L1 progeny which could not ingest the yeast cells. To test this, the previous experiment was repeated except that the worms were fed Fluorescein labeled yeast. The yeast was labeled with FITC and observed as detailed in Materials and Methods. *C. elegans* grown on fluorescent *S. cerevisiae* were able to ingest the labeled yeast at the L2-L3 and adult stages. No ingested yeast were observed in the L1-sized worms suggesting that the L1 larvae were unable to ingest yeast.

Antibiotics do not Affect *C. elegans*:

In the initial test, yeast plates contained the antibiotics Ampicillin and Gentamicin, while the *E. coli* plates did not. To test whether the antibiotics were resulting in growth arrest for the worms, an *E. coli* OP50 spot was put on a plate with antibiotics.

A concentrated slurry was made by centrifuging 1 mL of the *E. coli* broth culture, and then resuspending it in 100 μL of M9 buffer. The *E. coli* was concentrated to ensure ample food for the worms on plates where it is unable to grow with antibiotics present. The plate was then spotted with 10 μL of the concentrated slurry. In addition, 10 μL of yeast (RPY101) was spotted on an antibiotic plate as a control. The next day, ten adult worms were placed on to each plate, and the plates were incubated at 20° C. overnight. After the first twenty-four hours, the ten adult worms were removed from the plate to ensure that the L1's that would hatch from the eggs would be of relatively the same age. The plates were observed over another twenty-four hour period. Worms grew normally on the antibiotic plates and did not arrest developmentally.

The presence of antibiotics was optimal because it helped to control contamination by bacteria, other than *E. coli*, that could potentially obscure results. Antibiotics also helped to regulate the ratio of the yeast to bacteria in the mixture. The antibiotics were also demonstrated to have no harmful effects on the worms.

Egg Prep:

Because the arrested L1 larvae in initial tests developed in mothers who also were cultured on yeast plates, the arrest might have been an indirect result of an effect on the mother. To eliminate this variable, some yeast plates were started with eggs prepared by bleach treatment from worms cultured on NGM/*E. coli* OP50 plates. Worms hatched from these eggs arrested growth at the L1 stage (Table 4), similar to the results obtained when the plates were started with L3-L4 worms (Table 3).

For the larvae test, three plates were spotted, each with 20 μL. One was spotted with 100% *E. coli*, one with 100% yeast (RPY101), and the third with 50% of each, which was made from a mixture of 10 μL of each culture. After the spotted plates dried overnight, ten L3/L4 age worms were placed on to each of the three plates. After twenty-four hour incubation at 20° C., the adults were removed from the plates. The plates were observed for the following three days by counting the number of eggs and worms present each day. These data were compared to the number of eggs and worms that arose on plates seeded with eggs (prepared as described in section 2.5). For the egg prep test, three plates with identical characteristics were spotted.

TABLE 3

L3/L4 Count Test.

|  |  | Day 1 | Day 2 | Day 3 |
| --- | --- | --- | --- | --- |
| *E. coli* | Egg | 75 | 0 | 0 |
|  | L1 | 0 | 100 | 0 |
|  | Worm | 0 | 0 | 100 |
|  | Total | 75 | 100 | 100 |
| 50% Mixture | Egg | 30 | 0 | 0 |
|  | L1 | 1 | 0 | 0 |
|  | Worm | 0 | 70 | 100 |
|  | Total | 31 | 70 | 100 |
| Yeast | Egg | 40 | 3 | 0 |
|  | L1 | 0 | 20 | 1 |
|  | Worm | 0 | 0 | 0 |
|  | Total | 40 | 23 | 1 |

Three plates were spotted, each with 20 μL. One was spotted with 100% *E. coli*, one with 100% yeast (RPY101), and the third with 50% of each, which was made from a mixture of 10 μL of each culture. After the spotted plates dried overnight, ten L3/L4 age worms were placed on to each of the three plates. After twenty-four hour incubation at 20° C., the adults were removed from the plates. The plates were observed for the following three days by counting the number of eggs, L1 stage larva, and various stage worms larger than L1 stage present each day.

TABLE 4

Egg Prep Count Test.

| | | Day 1 | Day 2 | Day3 |
|---|---|---|---|---|
| E. coli | Egg | 36 | 0 | 0 |
| | L1 | 0 | 0 | 0 |
| | Worm | 0 | 36 | 50 |
| | Total | 36 | 36 | 50 |

TABLE 4-continued

Egg Prep Count Test.

| | | Day 1 | Day 2 | Day3 |
|---|---|---|---|---|
| 50% | Egg | 50 | 0 | 0 |
| Mixture | L1 | 0 | 0 | 0 |
| | Worm | 0 | 30 | 30 |
| | Total | 50 | 30 | 30 |
| Yeast | Egg | 60 | 5 | 0 |
| | L1 | 0 | 55 | 13 |
| | Worm | 0 | 0 | 0 |
| | Total | 60 | 60 | 13 |

Three plates were spotted, each with 20 μL. One was spotted with 100% E. coli, one with 100% yeast (RPY101), and the third with 50% of each, which was made from a mixture of 10 μL of each culture. After the spotted plates dried overnight, the plates were seeded with eggs (prepared as described in section 2.5). The plates were observed for the following three days by counting the number of eggs, L1 stage larva, and various stage worms larger than L1 stage present each day.

The results were that the worms on the yeast plate were arrested at L1 stage and the worms on the 1:1 yeast:E. coli mixture and E. coli plates were of various stages of development including adults. The growth arrest of L1s on the 100% yeast plates might have been the result of inability of the small L1 larvae to ingest yeast. However, when cultures on yeast plates were started with eggs picked from NGM/E. coli OP50 plates (data not shown), growth arrest was not observed. Therefore it was hypothesized that picking eggs from stock plates carried over some E. coli OP50 which was then available for L1s to eat. Once they grew past the L1 stage, they were able to eat the yeast.

Figure 5:
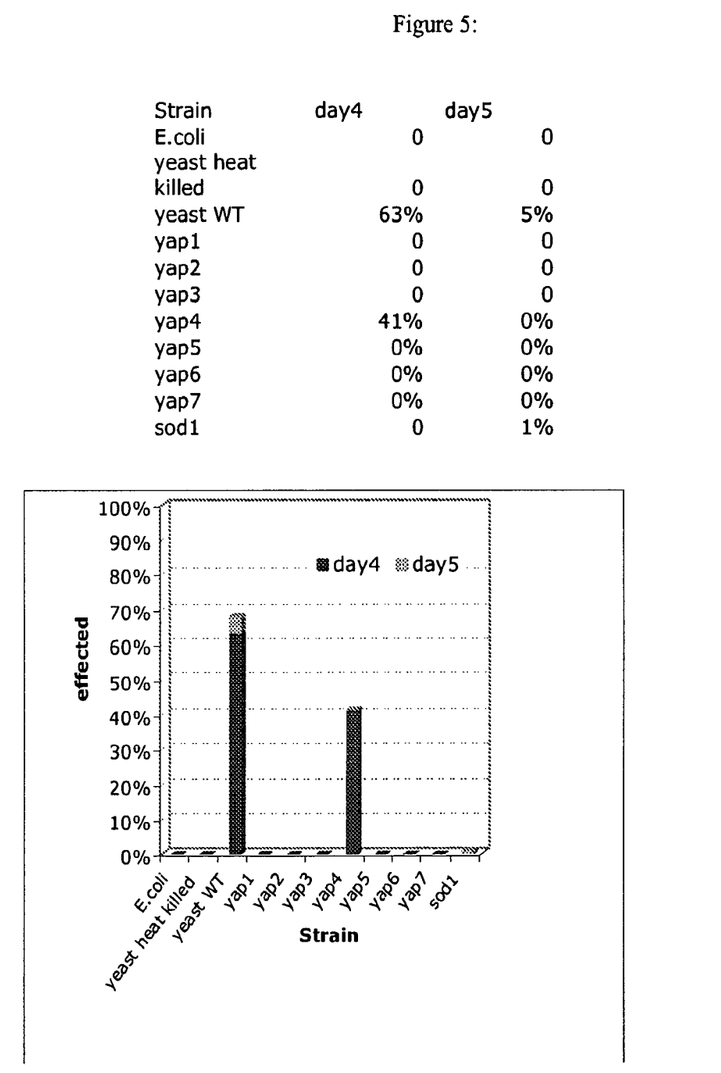
FIG. 5 is a Table and bar graph depicting the results of an assay in which *C. elegans* were co-cultured with yeast having mutations in the specified yap genes.

90% Percent S. cerevisiae and 10% E. coli OP50:

To test the optimal ratio of S. cerevisiae and E. coli provided as a food source for the worms, plates were prepared containing percentages of yeast from 0% to 100%, in 10% increments. Eggs were added using the egg prep procedure. The plates were observed for three days by counting the number of eggs and worms on each of the plates. On plates containing 0-60% yeast, numbers of worms per plate were relatively consistent over a three day period. In contrast, the number of worms on 70-100% yeast plates decreased strikingly over three days, in some cases to 50% of the eggs counted on day one (Table 5 and 6 and FIG. 5).

TABLE 5

Egg Prep and 10% Intervals (0-100%).
Table 1: Egg Prep and 10% Intervals (0-100%)

| Amount of Yeast (%) | Day 1 | | | Day 2 | | | Day 3 | | |
|---|---|---|---|---|---|---|---|---|---|
| | EGG | WORM | TOTAL | EGG | WORM | TOTAL | EGG | WORM | TOTAL |
| 0 | 93 | 0 | 93 | 9 | 90 | 99 | 9 | 75 | 84 |
| 10 | 100 | 0 | 100 | 1 | 75 | 76 | 1 | 92 | 93 |
| 20 | 60 | 0 | 60 | 7 | 90 | 97 | 1 | 93 | 94 |
| 30 | 55 | 0 | 55 | 4 | 100 | 104 | 4 | 90 | 94 |
| 40 | 50 | 0 | 50 | 2 | 80 | 82 | 3 | 75 | 78 |
| 50 | 150 | 0 | 150 | 17 | 200 | 217 | 20 | 160 | 180 |
| 60 | 30 | 0 | 30 | 3 | 29 | 32 | 3 | 34 | 37 |
| 70 | 65 | 0 | 65 | 6 | 60 | 66 | 2 | 47 | 49 |
| 80 | 65 | 0 | 65 | 8 | 55 | 63 | 8 | 38 | 46 |
| 90 | 65 | 0 | 65 | 4 | 50 | 54 | 4 | 25 | 29 |
| 100 | 90 | 0 | 90 | 7 | 40 | 47 | 6 | 30 | 36 |

TABLE 6

The Percentage of Total Column in Table 5 using Day 1 Total as 100%.

| | Day 1 | Day 2 | Day 3 |
|---|---|---|---|
| 0 | 100% | 100% | 90% |
| 10 | 100% | 76% | 93% |
| 20 | 100% | 100% | 100% |
| 30 | 100% | 100% | 100% |
| 40 | 100% | 100% | 100% |
| 50 | 100% | 100% | 100% |
| 60 | 100% | 100% | 100% |
| 70 | 100% | 100% | 75% |
| 80 | 100% | 97% | 71% |
| 90 | 100% | 83% | 45% |
| 100 | 100% | 52% | 40% |

From the 0% yeast and 100% yeast plates, worms were harvested on Day 4 and photographed in a compound microscope. Although adults were empirically larger than L1's they were smaller than expected for full-sized adults due to the fact that by Day 4 all of the E. coli food had been consumed and worms were starved.

The worms were placed on a 2% agarose pad with 1:100 dilution of azide on a slide with 3 μL, of M9 buffer to moisten the pad. The scale bar in the left box panel is 100 μm in length.

Figure 3:
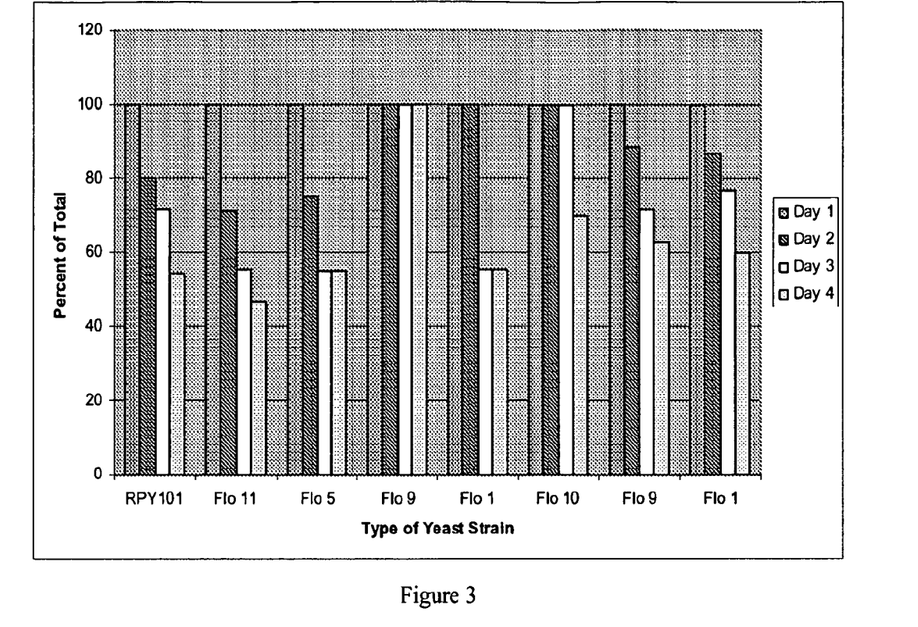
FIG. 3 is a bar graph of % Total compared to the amount of Total Eggs on Day 1.

Yeast Mutants:

Studies have been performed with two gene families. The Flo gene family encodes cell surface glycoproteins involved in the pathogenic response of yeast. The yeast Flo mutants were screened to be able to determine whether they affected C. elegans differently than wild-type yeast. The mutants were screened using the assay described in the five-day scheme described below. This also served as a way to test our assay. The yeast mutants were mixed with E. coli OP 50 at a ratio of 90:10. The plates were started with eggs that were isolated by bleach treatment and observed over a period of 4 days. The count of worms for each day can be seen in Table 7. The general trend was that the number of worms left on the plate as of Day 4 was 40-60% less than the amount of eggs from Day 1. The results are presented in FIG. 3.

The second gene family is the Yap gene family. This family of transcription factors are present only in fungi, which makes them good drug targets for antifungal therapy. The results are presented in FIG. 5.

The worms can be placed on a 2% agarose pad with 1:100 dilution of azide on a slide with 3 μL of M9 buffer to moisten the pad.

Worm Mutants:

The worm mutants were grown on *E. coli* OP 50 plates and the eggs were isolated by a bleach treatment. The eggs and hatched worms were observed and counted every day for eight days. Results are shown in Table 9. The worms on 90% yeast plates grew much slower than wild-type worms on a plate with *E. coli*/OP 50, under standard conditions, which take 42 hours from hatching to reach adulthood. Of the 10 strains of mutants tested, 7 strains of worms on the yeast plates reached adulthood in approximately 144 hours, or 6 days (3 generations). From day 6 on, it was observed that 3 worm mutant strains were still present as small larvae and were not growing. Three types of mutant *C. elegans*: DC 6 srf-3 (br6), DC 2 bus-17 (br2), and srf-6 (yj13) were arrested as small larvae 1 and did not produce offspring after 10 days of observation.

Figure 4:
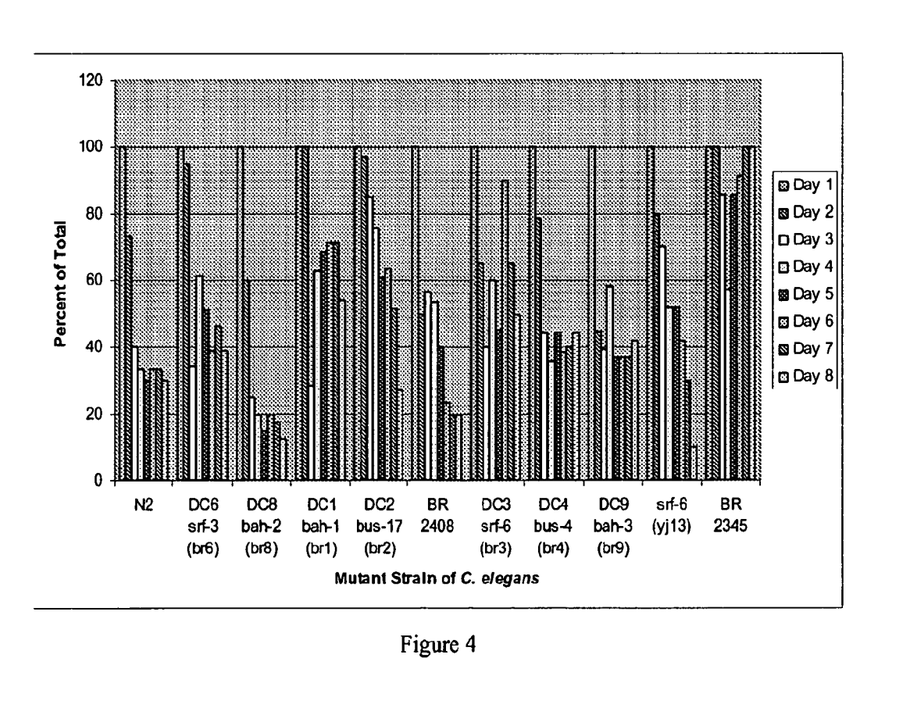
FIG. 4 is a bar graph of % Total compared to the amount of Total Eggs on Day 1.

The results from the worm mutants also show a decrease in number of worms from the number of eggs initially placed on the plate except for BR 2345. The results are presented in FIG. 4 as a bar graph representation.

The goal of our project was to develop an assay to study host-pathogen interactions between *C. elegans* and *S. cerevisiae*, which will be used to screen both *C. elegans* mutants and the *S. cerevisiae* gene-targeted deletion library. This study will give an opportunity in which to identify host and virulence factors in pathogenesis.

The protocol for the five-day scheme was developed to enable future researchers to reproduce the experiments performed and to screen a library of yeast mutants as well as *C. elegans* mutants. This will allow us to identify critical host factors and virulence factors important in the infection. This screening process was initiated in testing the assay. The assay can be set up in four days with an additional ten days for observation. All conditions used in the assay are based on experiments that were completed in this pathogenesis study.

The conditions that were optimized for the assay were as follows: the ratio of *S. cerevisiae* to *E. coli* provided as the nematodes' food source, the presence of the antibiotics, Ampicillin and Gentamicin, and the use of egg preparations.

There are several possible reasons for the L1 arrest; first that the L1 mouths are too small, second it was caused by the antibiotics, third that yeast actually causes the arrest (developmentally). Fluorescently labeled yeast was provided to the worms to ensure that they were in fact ingesting the yeast. Yeast was seen in the lumen of L2 to adult stage worms, but not in L1 sized worms. The simplest explanation for the apparent arrest of L1s on yeast plates is that L1s were unable to ingest yeast cells (~10 μm) because their mouth openings are too small.

The 90% *S. cerevisiae* and 10% *E. coli* mixture provided L1 stage worms with a bacterial food source that they are able to eat, rather than a 100% yeast food source that L1 worms are suspected to be physically unable to consume. This allowed the possible effects of fungal infection to be observed but still allowed L1 stage worms to develop into adults. This was important because it allowed worms to overcome the L1 arrest. Previous studies of bacterial pathogenesis have shown that bacteria can elicit a defensive response from *C. elegans* even when mixed with *E. coli* on assay plates (Nicholas and Hodgkin, *Curr. Biol.* 14:1256-1261, 2004; Gravato-Nobre et al., supra).

Egg preparations produced a large number of eggs, which allows testing of various mutants of yeast and worms. It is also less laborious than picking worms to each assay plate using a platinum wire tool. This also eliminates previous problems such as the accidental transfer of *E. coli* to a yeast plate.

Tail Swelling was observed in *C. elegans*, grown on plates containing yeast. This was reproduced once in a subsequent experiment. This phenotype was previously observed in *C. elegans* infection by the bacterium *M. nematophilum* (Hodgkin, Kuwabara, and Corneliussen, *Curr. Biol.* 10:1615-1618, 2000). The tail swelling response in the worm results from an innate immune response to pathological infection preventing further constipation or infection in the worm, or death (Nicholas and Hodgkin, 2004).

Mutants of *S. cerevisiae* and *C. elegans* were tested once the assay had been developed using wild type N2 worms, to initiate the screening process and observe potential effects on *C. elegans* phenotypes. Mutants were also used to test the efficiency of the current assay. The yeast mutants tested all caused an anal swelling in worms after ten days of observation. It was expected that all three mutant types, surface (srf), bacterial unswollen (bus) and bacterial adhesion (bah) would show increased resistance to the pathogen and therefore resistance to an infection.

In future experiments, we recommend testing grinder defective mutants of *C. elegans* as the grinder is the nematodes' second physical line of defense (Alegado et al., supra). The fact that the mechanism of the grinder is not as efficient may have an increased effect, causing the effect on these mutants to be lethal to the worm due to the inability to break up particles that the worm is ingesting and may allow for increased probability of colonization of the worms digestive tract (from the mouth to anus). One deficiency in the assay is its scale-up ability. Using NGM agar plates may not be efficient to screen the *S. cerevisiae* gene-target deletion library. The procedure could be modified to grow worms in liquid media, in microtiter plates. Another deficiency seen when testing the *C. elegans* mutants was that the number of worms recorded each day varied and decreased at each observation. This decrease in population posed the question of where the worms were crawling to, perhaps off the plate and why, as they do not do this on *E. coli* plates. The assay might be improved by culturing worms on 50% yeast:50% *E. coli*, which did not result in a decrease in worm numbers per plate. The reason for loss of worms at higher percentages of yeast should be investigated further.

A number of embodiments of the invention have been described. Nevertheless, it will be understood that various modifications may be made without departing from the spirit and scope of the invention. Accordingly, other embodiments are within the scope of the following claims.

The Five-Day Protocol:

The procedure should be done using sterile technique. The protocol is designed to be used to screen mutant strains of *C. elegans* and to screen the gene-targeted deletion library of *S. cerevisiae*. The procedure is approximately 4 days long, allowing for natural biological processes, and the protocol is grouped by each day. Some of the procedures in Day 1 only need to be done when supplies run out, after the initial preparation.

Day 1:

Start four stock plates of desired worms by placing three worms on an NG agar plate. Incubate at 20° C. and store in non-airtight container. Three liquid media are made as follows. YPD is made by combining 10 g bacto-yeast extract, 20 g bacto-peptone, and 20 g dextrose. The ingredients are dissolved in 500 mL of $rdH_2O$ and topped off to 1 L when dissolved. To make medium for plating, add 20 g agar. LB is made by combining 10 g bacto-tryptone, 5 g bacto-yeast extract, and 10 g NaCl. The ingredients are dissolved in 500 mL of $rdH_2O$ and topped off to 1 L when dissolved. The pH is adjusted to 7.5 with sodium hydroxide. Hershey Broth is made by combining 8 g nutrient broth, 5 g bacto-peptone, 5 g sodium chloride, and 1 g glucose. The ingredients are dissolved in 500 mL of $rdH_2O$ and topped off to 1 L when dissolved. The media can be autoclaved at 121° C. for 20 minutes.

NG agar plates are also made on the first day by preparing media (2 100 mL aliquots) of:
  i. 0.3 g NaCl
  ii. 2.0 g Bacto-agar
  iii. 0.25 g Bacto-peptone
  iv. 97.5 mL Water
  *Autoclave 121° C. for 30 minutes
  **Autoclave repeat syringe and tubing—pre-set to 2 mL
  v. Add Salts (Sterile Stocks)
    1. 100 µL 1M $CaCl_2$
    2. 100 µL 1M $MgSO_4$
    3. 2.5 mL 1M $KPO_4$
    4. 100 µL Cholesterol in Ethanol (do not flame)
  vi. Add Antibiotics to one flask
    1. 200 µg/mL Ampicillin
    2. 15 µg/mL Gentamicin For 35 mm plates, one can use about 2 mL per plate. The plates can then be stored in an airtight container with moist paper towel at 20° C.

Other activities on Day 1 include autoclaving: (1) a 500 mL beaker of 1.5 mL Eppendorf tubes, (2) M9 buffer (6 g $Na_2HPO_4$, 3 g $KH_2PO_4$, 5 g NaCl, and 0.25 g $MgSO_4.7H_2O$ dissolved in 1 L $rdH_2O$), and (3) PBS.

YPD agar plates are streaked with a desired yeast strain from the library; and incubated inverted and parafilmed at 30° C. overnight. NG agar plates are streaked with OP50.

Day 2:

To generate four stock plates of desired worms, place three worms on an NG agar plate, incubate at 20° C., and store in non-airtight container. To make liquid cultures for yeast, place 5 ml of YPD in glass test tube, pick one colony into the liquid using a sterile toothpick, and incubate with rotation at 30° C. overnight. For E. coli, the procedure is the same except incubation is carried out at 37° C. overnight.

Day 3:

Make four stock plates of desired worms, as described above. Prepare a mixture of 90% Yeast/10% E. coli by vortexing each 5 mL culture started on Day 2 and adding 18 µL of the yeast culture and 2 µL of the E. coli to sterile 1.5 mL Eppendorf tube. Vortex the mixture and spot each plate with 20 µL of the mixture. The culture stocks can be stored at 4° C. after use.

Day 4:

Make four stock plates of desired worms, as described above. For egg preparation: (1) make a bleach solution (0.5 g NaOH in 50 mL of [12.5 mL bleach and 37.5 mL water]); (2) Wash four stock plates with M9 buffer to wash worms and eggs off the plate, collect the washes in a 15 mL conical tube, and top of with M9 buffer to 12 mLs; (3) centrifuge the 15 mL conical tubes at 900×g (2000 rpm) for 2 minutes, aspirate the supernatant, resuspend the pellet in M9 buffer to 12 mL, repeating once; (4) add the bleach solution, resuspending up to 12 mL, invert gently for 3 minutes, and centrifuge for 2 minutes at 2000×g (3000 rpm); and (5) wash with M9 Buffer, aspirate the supernatant, resuspend the pellet to 12 mL with M9 buffer, centrifuge for 2 minutes at 2000×g (3000 rpm), repeating twice, and resuspend the final pellet to 2 ml in M9 buffer. To test the egg concentration, place 5 µL of egg solution on an empty stock plate and count the number of eggs under a microscope. If there are more than 30 eggs, dilute the solution with more M9 buffer. If there are less than 30 eggs, centrifuge and resuspend the eggs in less M9 buffer. To generate mixed cultures, place 5 µL of the egg suspension (~30 eggs) on to each experimental plate, outside the yeast/E. coli mixture spot. Count the number of eggs and record.

Day 5 and Onward:

To maintain stocks of worms for egg preparation, stock plates of worms can be prepared daily as described above. The number of eggs is counted and recorded.

Example 2

Genes that are unique to fungi are potential targets for antifungal agents. It has been suggested that Yap1, a fungal-specific transcription factor, is involved in pathogenesis (7-9). We have now developed an assay to demonstrate that Yap1 is required for fungal pathogenicity in a nematode model. We believe the regulation of oxidative stress is important for fungal pathogenesis, and we are interested in identifying agents that impede pathogenesis by dysregulation of oxidative stress. This pathway has not yet been targeted for antifungal drug therapy. Since its regulation in fungi occurs via a unique transcription factor, it is an attractive target for drug development. In addition, our assay can be used to identify other fungal virulence factors as well as host factors unique to fungal infections. We will: (A) analyze yeast mutants to more clearly define the fungal factors involved; (B) address whether reactive oxygen species (ROS) are produced by C. elegans when exposed to S. cerevisiae; and (C) test whether production of ROS by the host is required to combat fungal infection. Our results will help establish the validity of genes (like YAP1 and YAP2) in this pathway as anti-fungal drug targets.

Figure 6A:
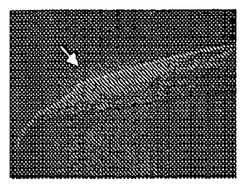
FIGS. 6A and 6B are photomicrographs showing the deformed anal region (Dar phenotype) in *C. elegans* that ingest *S. cerevisiae* (panel 6A, marked with an arrowhead). The same region in worms that ingest *E. coli* alone are shown in panel 6B.
Figure 6B:
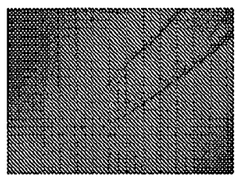

C. elegans that are reared on mixed lawns of E. coli (strain OP50) and S. cerevisiae (strain S288c, BY4741) at a 3:1 ratio by weight (an estimated 30:1 ration by number of organisms), exhibit the deformed anal region (Dar) phenotype (FIG. 6). This phenotype, first described as a disease symptom of worms infected with Microbacterium nematophilum (5), is characterized as a distinctive swelling in the post anal region.

As we discovered that yeast cells are too large for the young larvae to ingest, we provided E. coli as a nutritional source. The worms are carefully monitored twice a day from the time the eggs are exposed to the microbial cultures up to day 4, when the Dar phenotype is clearly visible. As early as day 2, the worms that experienced mixed lawns of E. coli and S. cerevisiae appear thin and more sluggish as compared to worms that were plated on pure E. coli lawns. By day 3, the worms have a distended intestine, presumably a sign of constipation (5). At day 4, the anal swelling (or Dar) phenotype is scored for worms plated on mixed lawns of E. coli and yeast and compared to worms plated on E. coli lawns without yeast or with heat inactivated yeast. We found that worms experiencing trace amounts of yeast are affected by the disease and only metabolically active yeast cells are capable of causing disease.

To test whether the Dar phenotype was reversible, we transferred the affected worms to plates containing a pure lawn of *E. coli*. The worms were 'cured' within 2 days of transfer and the anal swelling was no longer visible. This strongly supports the notion that yeast cause the anal swelling.

Even though most of the experiments were terminated at day 4, worms were monitored past this time. By day 5, some animals died. Because the life span of *C. elegans* is approximately 14 days, their deaths were not due to normal aging.

As a result of vulval swelling, the progeny of the dead worms hatched inside the animals. Thus, viable *S. cerevisiae* causes an infection in at least two of the three mucosal orifices of *C. elegans* (the anal cavity and vulva region). This is reminiscent of the most frequently identified location for fungal infections in mammals.

We have since tested other popular laboratory yeast strains such as Σ1278b in this assay. Interestingly, the Σ1278b strain results in nematode death before we observe the Dar phenotype. We believe this is because unlike the S288c, BY4741 strain, Σ1278b can undergo dimorphic transition from yeast to pseudohyphae, an important characteristic of feral strains of *S. cerevisiae* and other pathogenic fungi (10). For the purposes of this study we chose to use BY4741 because: (i) this is the strain whose genomic sequence is available and is the wild type parent for the whole genome deletion collection making it amenable to a systematic screen of fungal virulence factors and (ii) the milder phenotype with several visible stages of "disease" progression will allow us to identify genes that both increase as well as abolish the pathogenic response.

In a preliminary experiment, we chose to test yap1Δ and its paralog yap2Δ in this assay. Yap1 is a fungal transcription factor. An ortholog has been identified in most fungi whose genome has been sequenced but not in any other organisms including humans. It has recently been shown that Yap1 is activated in conidial germ tubes of *Cochliobolus heterostrophus*, a fungal pathogen of maize, at the earliest stage of plant infection and persists during infection (7). Furthermore, overexpression of CAP1 (the *C. albicans* ortholog of YAP1) confers resistance to the popular clinical antifungal fluconazole, an azole derivative (11). These properties make it a likely candidate for antifungal drug development.

*C. elegans* exposed to mixed lawns containing *E. coli* and either yap1Δ or yap2Δ mutants failed to exhibit the Dar phenotype. As a control, we used a mutant in a related a transcription factor, Yap4, whose Dar phenotype is indistinguishable from wild type. These results strongly support the notion that Yap1 is an important virulence factor for fungal pathogenesis. Accordingly, screens for inhibitors of Yap1 are within the scope of the present invention, and chemical agents or small molecules that inhibit Yap1 function would clearly be attractive for antifungal drug development.

In addition to the regulation of oxidative stress responses, Yap1 plays a role in regulating multidrug resistance (8, 11). To define which aspect of Yap1 is required to evoke the Dar response, we tested mutants that were defective in one or the other response but not both. The specific mutants tested were Superoxide dismutase (sod1Δ) and Pleotropic Drug resistance (pdr1Δ, pdr15Δ) genes using the same assay. The physiological role for Sod1 is to guard cells against oxidative damage by neutralizing reactive oxygen species (12-14). Pdr1, like Yap1, is a transcription factor, and regulates resistance to a variety of drugs while PDR15 encodes an ATP binding cassette (ABC) transporter of the plasma membrane implicated in general stress response factor and cellular detoxification (15-19). Like yap1Δ and yap2Δ mutants, sod1Δ mutants also fail to elicit a robust Dar response while pdr1Δ and pdr15Δ mutants are indistinguishable from their wild-type counterparts. These results eliminate the possibility that multi drug resistance is required during virulence. Instead, they suggest that resistance to oxidative stress is required to cause disease in the nematodes.

The results described above indicate that the fungal specific transcription factors, Yap1 and Yap2, are required for virulence. These proteins mediate oxidative stress responses and pleotropic drug resistance. Using mutants that are defective in only one of these two pathways, we believe that the inability of Yap1 mutants to tolerate oxidative stress makes them avirulent. Using a variety of powerful tools available in yeast and worms we propose to further test the hypothesis that oxidative stress plays an important role in fungal pathogenesis. Through the studies described below we can, first, further test the hypothesis that fungal resistance to oxidative stress and host production of ROS is an important aspect of fungal pathogenesis; second, conduct a whole genome screen to identify novel virulence factors in the model fungal pathogen *S. cerevisiae*; and third, test the role of specific host factors in fungal pathogenesis.

To further investigate whether the inability to elicit the Dar phenotype is restricted to mutants compromised in oxidative stress response, we will test if yeast mutants, sensitive to other stresses, are also compromised in the Dar response. We will start with two broad classes of mutants: (i) those that regulate general stress response such as msn2Δ, msn4Δ and msn2Δmsn4Δ and (ii) another that is involved in regulating Osmotic stress resistance, osr5Δ.

These mutants will be retrieved from the yeast deletion library and be checked for the Kanamycin resistance gene that marks the deleted locus using PCR. Simple phenotypic tests, such as sensitivity to heat shock or ability to grow on glycerol will be performed to further confirm the mutations.

The assay will be performed as described above. We anticipate that the OSR mutant will be able to elicit the Dar phenotype in the nematodes and, in that respect, be indistinguishable from the wild-type control yeast strains. The msn2Δ and msn4Δ mutants regulate a variety of stress responses including oxidative stress. Although their behavior is hard to predict, we are encouraged by the effect of pdr15Δ because it is peripherally involved in general stress response and is still able to evoke the Dar phenotype. If the msn mutants cause the Dar phenotype, it will strongly support our hypothesis that resistance to oxidative stress is exclusively important for fungal pathogenesis.

The msn2Δmsn4Δ double deletion mutant is especially compromised and may not be able to show the Dar phenotype because of its general lack-of-fecundity. In spite of this, we feel that the mutants are worth testing to further challenge our hypothesis. A positive result will exclude the involvement of a variety of stresses in fungal infections. Alternate and complementing approaches are presented below.

We have identified that yeast mutants that are unable to withstand oxidative stress are avirulent in *C. elegans*. This suggests that fungi involved in a pathogenic relationship with nematodes encounter reactive oxygen species (ROS) that they must overcome in order to cause disease. This presents a testable hypothesis that the nematode is creating a hostile oxidative environment for the pathogen. It has recently been shown that *C. elegans* produce ROSs when infected with bacteria such as *E. faecalis, E. faecium* and *S. aureus* (20, 21), presumably as a part of their defense mechanisms. Therefore we propose to test for ROS production in *C. elegans* when exposed to *S. cerevisiae*.

Two assays have previously been described to test for the production of ROS (20). First, a colorimetric peroxidase activity assay and second, microscopic observation of the accumulation of lipofuscin, a fluorescent compound that accumulates in *C. elegans* intestinal cells experiencing oxidative damage. We are encouraged by our initial observation of increased fluorescence in the intestinal cells of infected worms.

a) Peroxidase enzyme activity: A commercially available assay (Amplex Red peroxidase kit, Molecular Probes) will be used to test peroxidase activity (20). Briefly, ROS produced by the worms, presumably in response to pathogenic attack, oxidize the substrate Amplex Red, to form a red fluorescent product that can be measured spectrophotometrically. Increased peroxidase activity upon exposure to yeast would support our hypothesis but a negative result will be inconclusive.

b) Accumulation of lipofuscin: Worms experiencing oxidative damage accumulate a fluorescent compound, lipofuscin in their intestine. Therefore we can compare the level of fluorescence between worms reared on *E. coli* versus worms reared on mixed cultures of yeast and *E. coli* to assess the extent of oxidative damage. Our initial observations indicate that we indeed observe increased fluorescence in the intestinal cells of the nematodes that ingest *S. cerevisiae* but more careful and controlled experiments need to be conducted to verify this preliminary observation.

Determining the Role of Host Oxidase in Fungal Pathogenesis:

To determine whether BLI-3 is responsible for generating an environment of elevated ROS, we obtained the bli-3 (or Blister-3) allele from the *C. elegans* stock center. This is a point mutant generated by EMS mutagenesis and shows the appropriate (blister) phenotype. The test will be performed as outlined in the Table immediately below.

TABLE

| C. elegans S. cerevisae | Bli-3 | Sod-3 (overexpression) | N2 WT (control) |
|---|---|---|---|
| BY4741 WT | TBD | TBD | Dar phenotype observed |
| yap1Δ | TBD | TBD | Dar phenotype NOT observed |
| sod1Δ | TBD | TBD | Dar phenotype NOT observed |
| E. coli (control) | Dar phenotype NOT observed | Dar phenotype NOT observed | Dar phenotype NOT observed |

(TBD—to be determined).

The assay will be performed as described above and outlined in the Table above. If bli-3 is required for resistance to fungal pathogenesis, we expect to see the Dar phenotype produced even by the yap1Δ and sod1Δ mutants, which are incapable of eliciting Dar in wild-type *C. elegans*. Moreover, we might expect to see a more severe infection of bli-3. If no phenotypic changes are observed, the experiment will be inconclusive.

The bli-3 mutation is pleotropic. It derives it name from the appearance of blisters on the cuticle of the mutant worms. This is because the bli-3 catalyzes the cross-linking of tyrosine residues involved in the stabilization of cuticular extracellular matrix (24). This is consistent with the identification of bli-3 as CeDuox1 because RNAi knockdown of the latter also produces a blister phenotype. In its absence, the cortical layer of the cuticle detaches from the basal layer below, forming blisters. This might result in failure of yeast cells to recognize sites of attachment in the cuticle, or alternatively, allow easier penetration of yeast cells into the tissues. Thus both positive and negative results would be complicated by this pleotropy. The three following alternate experiments will be performed to address this.

Other Mutants:

There are five other bli mutants that do not play a role in formation of ROSs but compromise the cuticle. To test whether host ROS production resists fungal pathogenesis we will test few other selected bli mutants. This experiment will be performed similar to the one outlined in Table 1. Here we expect to observe the Dar phenotype only when the worms fed with wild-type yeast but not when they are fed yap1Δ or sod1Δ mutants. These mutants might yield the Dar phenotype because of a compromised cuticle.

Chemical Inhibition of ROS Production:

Diphenylene iodonium sulfate (DPI) is a known inhibitor of NADPH-oxidase activity and has recently been shown to inhibit production of ROS in nematodes (20). Briefly, worms reared on mixed cultures of mutant or wild-type yeast with *E. coli* will be treated with DPI. Its effect on the nematode host will be observed phenotypically (using the Dar phenotype described in Preliminary studies) and biochemically (using the peroxidase assay described in Specific Aim 1B). If ROS production is an important aspect of the host defense mechanism, we expect to observe the Dar phenotype and low peroxidase activity in both cases because the host defenses are artificially compromised.

Overexpression of Sod-3 in *C. elegans*:

A transgenic *C. elegans* strain overexpressing sod-3 is more susceptible to *E. faecis* infection than wild type (20). We will obtain this strain (20) and test it for susceptibility to *S. cerevisiae*-caused disease. If it is more susceptible it would suggest that ROS are required for the immune response to *S. cerevisiae*.

Identifying Novel Genes and Pathways as Potential Targets for Antifungal Therapy:

*S. cerevisiae*, although not normally a human pathogen, exhibits several traits such as substrate adhesion and dimorphic transition, typical of pathogenic fungi (25). *S. cerevisiae* has withstood the test of time as a general model for higher eukaryotes and for pathogenic fungi in particular. For example, *S. cerevisiae* uses several conserved pathways to regulate dimorphism, which have also been identified in other pathogenic fungi such as *C. albicans*, a human opportunistic pathogen (26, 27) and *U. maydis*, the etiological agent of corn smut disease (28, 29). More importantly the plethora of tools available and ease of manipulation make it the only fungus in which such studies are feasible.

It is very difficult to medically treat a systemic fungal infection once it has been established in the host organism. For humans, only a few anti-fungal agents exist, and these have unpleasant side effects. In addition, developing anti-fungal agents or understanding the molecular basis behind pathogenic fungi is often difficult and expensive. Hence there is a growing need for simple and innovative systems to explore fungal virulence strategies and assay the contribution of individual genes to pathogenesis.

*S. cerevisiae* is the only fungus that has a whole genome deletion library. This unique tool makes it possible to conduct a comprehensive screen for virulence factors thereby pushing the boundaries of innovative research. We have begun pilot screens with small gene families to assess the feasibility of a large-scale whole genome screen and anticipate that it will take a year to complete the primary screen. The yeast deletion library consists of approximately 5100 clones represented in 51, 96 well plates. The pathogenesis assay for each library plate will be done in two, 48 well culture plates. At maximum efficiency we can process 2-3 plates a week therefore a conservative estimate of 1 plate per week will enable us to complete the screen in one calendar year.

We have begun pilot screens with small gene families to evaluate the likely candidates. Whether or not these pathways make good targets for antifungal agents is yet to be determined. However already Yap1 and Yap2 show tremendous potential.

We have the *S. cerevisiae* genome deletion collection and will screen it for mutants that produce a different effect on *C. elegans* than that produced by their wild-type counterpart. Severity will be scored as a function of percentage of affected worms and time of appearance of the Dar phenotype or even time of death as in the case of Σ1278b. A genomic deletion library is being constructed in the Σ1278b background, which we plan to obtain and screen at a later date. However using the S288c genomic deletion library allows us to look for more severe as well as less severe effects on *C. elegans* for the reasons mentioned earlier.

Identifying Novel Host Factors that Play a Critical Role in Fungal Pathogenesis:

For a fuller understanding of the host-pathogen interaction, it is necessary to identify host factors which are essential for resistance to pathogen.

A large number of *C. elegans* mutants are available from the *Caenorhabditis* Genetics Center as well as from individual investigators. Mutants that are likely candidates for altered Dar response (see the Table below) will be tested using our standard assay. In preliminary experiments we have already identified a *C. elegans* mutant that fails to produce Dar when exposed to wild-type *S. cerevisiae*. A bus-4 (Bacterially Un-swollen) mutation completely abolished the Dar phenotype in our assay. Bus-4 is predicted to encode a galactosyltransferase (6, 32) that may be involved in glycosylation of *C. elegans* surface coat proteins. The bus mutants were discovered in screens for mutants that did not develop a Dar phenotype when exposed to the bacterium *M. nematophilum*, presumably because the mutations affected adhesion/recognition sites for the bacterium. Several other surface-altered *C. elegans* mutants that show a Bus phenotype on *M. nematophilum* have been tested; so far no others have eliminated the Dar phenotype on *S. cerevisiae*. Thus our preliminary tests suggest that host factors involved in fungal pathogenesis are not identical to those involved in bacterial pathogenesis, and that it will be worthwhile to continue these investigations of host factors specifically involved in fungal pathogenesis.

Two pair-wise comparisons will be made for each mutant. First, the phenotype of the mutant nematode and the cognate wild-type worm will be compared after exposure to *S. cerevisiae*. Second, the phenotype of the mutant nematodes on *S. cerevisiae* will be compared to the phenotype on *E. coli* alone. While there are some similarities between *M. nematophilum* and *S. cerevisiae* infection of *C. elegans*, our preliminary results lead us to believe that there is not be a complete overlap. Therefore while the *M. nematophilum* results will serve as a guide for initial selection of candidates, we expect to find a different set of requirements for the response to yeast infection. This will help determine whether there is a signature host response to fungal pathogenesis.

We can consider the infection of *C. elegans* by a microbial pathogen as a series of steps, including: 1) initial interaction either by ingestion or adhesion to the nematode surface; 2) proliferation on the surface or in a body cavity; 3) pathogenesis. The corresponding innate immune response of the nematode host include: 1) recognition of the pathogen; 2) triggering of effector responses by signal transduction; and 3) execution of anti-microbial responses. These considerations suggest some candidates for host genes to test including:

Nematode Genes Required for Surface Recognition:

The surface coat of *C. elegans* is a negatively charged glycoprotein-rich layer overlying the epicuticle. This layer is the nematode's first line of defense and believed to prevent predator adhesion. Several classes of srf (surface) mutants are available which alter surface composition and are also susceptible to microbial pathogens. As mentioned above, mutations in the bus genes result in the failure to produce a Dar phenotype when exposed to *M. nematophilum* (32). Finally, mutations in bah (bacterial adhesion) genes prevent formation of a biofilm by the bacterium *Yersinia pestis* (33, 34). We have already begun testing this class of mutants and preliminary results indicate that bus-4 abolishes the Dar phenotype (Percentage of worms showing Dar phenotype: bus-4=0, bus-17=52, Wild type=60).

Genes Involved in Signal Transduction Pathways:

Three MAPK pathways have been identified in *C. elegans*, the ERK, JNK and p38 MAPK pathways (35-37). The ERK MAPK pathway is required to prevent severe infection by *M. nematophilum* (38), while the p38 pathway including genes nsy-1, sek-1, and pmk-1 provides defense against infection by several different pathogenic bacteria (38, 39). The JNK pathway has been implicated in immunity in other organisms (40). We will test representative mutants in each of these MAP kinase pathways for effects on *S. cerevisiae* pathogenesis in *C. elegans*.

The signaling pathway controlled by the insulin-like receptor DAF-2 and the downstream transcription factor DAF-16 is involved in controlling longevity and stress responses (41). Daf-2 mutants are also resistant to killing by bacterial pathogens and daf-16 mutation prevents this resistance (3). We will test daf-2 and daf-16 mutants for increased or decreased pathology in the presence of *S. cerevisiae*.

A *C. elegans* TGF-β homolog, DBL-1, has been implicated in immune defenses in *C. elegans* (42). Mutants in dbl-1 and other downstream effectors in this pathway show decreased resistance to killing by *Serratia marcescens*. The TIR-1 (Toll-interleukin-1) receptor homolog in *C. elegans* has been shown to mediate resistance to infection by a filamentous fungus (35).

Effector Genes:

Several classes of immune effector molecules are upregulated upon contact with microbial pathogens. These include C-type lectins (CLEC family), antimicrobial peptides: galectins, thaumatins (THN-2), and lysozymes (LYS-7) (43). Several genes are also required to prevent pathogenesis by *M. nematophilum* (43). Since many of these genes have been implicated only by expression changes, null mutants do not exist. Therefore we will employ standard RNAi knockdown methods for this study. Briefly, *C. elegans* will be fed *E. coli* strains that express gene-specific double-stranded RNA in the presence or absence of *S. cerevisiae*. Worms will be scored for changes in the Dar phenotype or in other phenotypes as described above.

TABLE

| a) Altered Surface properties | b) Signal transduction | c) effector proteins |
|---|---|---|
| bah-1, bah-2 (2 alleles), bah-4 | nsy-1, jnk-1, mek-1, mek-2 | clec-67, clec-15, clec-60, clec-86 |
| bus-4, bus-17, | daf-2, daf-16 | srh-220, srh-222 |
| srf-2 (2 alleles), srf-3, srf-6 | dbl-1 | lys-7 |
| | tir-1 | thn-2 |

There clearly are other classes of mutants that may affect pathogen recognition and host defenses. For example, the nematode may use its chemical senses to recognize signals that a pathogen is present (44). Such mutants will be tested at a later date.

Attempts to identify unique effector factors for fungal pathogenesis by single gene inactivation may prove difficult because redundant multi-gene families encode many of these molecules. Moreover, multiple pathways are activated by a single pathogen. However, in spite of these difficulties a positive result would greatly advance our understanding of host response to fungal pathogenesis. An alternate approach to the above mentioned phenotypic studies will be to identify *C. elegans* genes reported in the literature that are upregulated in an infection and design qPCR probes to test them in our assay. Unfortunately these methods tend to test the likely candidates one-gene/pathway-at-a-time.

Using a hypothesis-driven approach the PI hopes to take full advantage of all of the genetic resources available such as genetic mutations, well-annotated genome sequence and extensive genome-wide expression studies. One tool that we have not utilized thus far is the RNAi library available for knocking down every single gene in *C. elegans*. In order to rapidly identify anti-fungal host factors, our innovative assay allows us to perform a high-throughput RNAi microtiter well screen of changes in *C. elegans* phenotypes in the presence of *S. cerevisiae*. Such a screen would take advantage of available RNAi feeding libraries. Although it is beyond the scope of this project it is important to note that such screens can be made systemic or can target double-stranded RNA expression to specific tissues.

1. R. P. Wenzel, *Clin Infect Dis* 20, 1531 (June, 1995).
2. F. G. Oppenheim et al., *J Biol Chem* 263, 7472 (Jun. 5, 1988).
3. D. A. Garsin et al., *Science* 300, 1921 (Jun. 20, 2003).
4. C. D. Sifri et al., *Infect Immun* 70, 5647 (October, 2002).
5. J. Hodgkin, P. E. Kuwabara, B. Corneliussen, *Curr Biol* 10, 1615 (Dec. 14-28, 2000).
6. M. J. Gravato-Nobre, J. Hodgkin, *Cell Microbiol* 7, 741 (June, 2005).
7. S. Lev et al., *Eukaryot Cell* 4, 443 (February, 2005).
8. A. M. Alarco, M. Raymond, *J Bacteriol* 181, 700 (1999).
9. R. Prusty, P. Grisafi, G. R. Fink, *Proc Natl Acad Sci USA* 101, 4153 (Apr. 23, 2004).
10. H. Liu, C. A. Styles, G. R. Fink, *Genetics* 144, 967 (1996).
11. A. M. Alarco, I. Balan, D. Talibi, N. Mainville, M. Raymond, *J Biol Chem* 272, 19304 Aug. 1, 1997).
12. O. Bermingham-McDonogh, E. B. Gralla, J. S. Valentine, *Proc Natl Acad Sci USA* 85, 4789 (July, 1988).
13. E. C. Chang, B. F. Crawford, Z. Hong, T. Bilinski, D. J. Kosman, *J Biol Chem* 266, 4417 (Mar. 5, 1991).
14. V. D. Longo, L. L. Liou, J. S. Valentine, E. B. Gralla, *Arch Biochem Biophys* 365, 131 (May 1, 1999).
15. A. Decottignies et al., *J Biol Chem* 273, 12612 (May 15, 1998).
16. I. Hikkel et al., *J Biol Chem* 278, 11427 (Mar. 28, 2003).
17. H. Wolfger, Y. Mahe, A. Parle-McDermott, A. Delahodde, K. Kuchler, *FEBS Lett* 418, 269 (Dec. 1, 1997).
18. H. Wolfger, Y. M. Mamnun, K. Kuchler, *Res Microbiol* 152, 375 (April-May, 2001).
19. H. Wolfger, Y. M. Mamnun, K. Kuchler, *J Biol Chem* 279, 11593 (Mar. 19, 2004).
20. V. Chavez, A. Mohri-Shiomi, A. Maadani, L. A. Vega, D. A. Garsin, *Genetics* (May 4, 2007).
21. T. I. Moy, E. Mylonakis, S. B. Calderwood, F. M. Ausubel, *Infect Immun* 72, 4512 (August, 2004).
22. B. M. Babior, J. T. Curnutte, B. J. McMurrich, *J Clin Invest* 58, 989 (October, 1976).
23. J. D. Lambeth, G. Cheng, R. S. Arnold, W. A. Edens, *Trends Biochem Sci* 25, 459 (October, 2000).
24. W. A. Edens et al., *J Cell Biol* 154, 879 (Aug. 20, 2001).
25. C. Gimeno, P. Ljungdahl, C. Styles, G. Fink, *Cell* 68, p 1077 (1992).
26. C. S. Hwang, J. H. Oh, W. K. Huh, H. S. Yim, S. O. Kang, *Mol Microbiol* 47, 1029 (February, 2003).
27. J. Chen et al., *Mol Cell Biol* 20, 8696 (December, 2000).
28. M. E. Mayorga, S. E. Gold, *Mol Microbiol* 34, 485 (November, 1999).
29. S. Gold, G. Duncan, K. Barrett, J. Kronstad, *Genes Dev* 8, 2805 (1994).
30. M. C. Lorenz, G. R. Fink, *Nature* 412, 83 (Jul. 5, 2001).
31. J. Breger et al., *PLoS Pathog* 3, e18 (Feb. 2, 2007).
32. M. J. Gravato-Nobre et al., *Genetics* 171, 1033 (November, 2005).
33. C. Darby et al., *Genetics* (Mar. 4, 2007).
34. J. Hoflich et al., *J Biol Chem* 279, 30440 (Jul. 16, 2004).
35. C. Couillault et al., *Nat Immunol* 5, 488 (May, 2004).
36. D. L. Huffman et al., *Proc Natl Acad Sci USA* 101, 10995 (Jul. 27, 2004).
37. D. H. Kim et al., *Science* 297, 623 (Jul. 26, 2002).
38. H. R. Nicholas, J. Hodgkin, *Curr Biol* 14, 1256 (Jul. 27, 2004).
39. A. Aballay, E. Drenkard, L. R. Hilbun, F. M. Ausubel, *Curr Biol* 13, 47 (Jan. 8, 2003).
40. C. Dong, R. J. Davis, R. A. Flavell, *Annu Rev Immunol* 20, 55 (2002).
41. K. Lin, J. B. Dorman, A. Rodan, C. Kenyon, *Science* 278, 1319 (Nov. 14, 1997).
42. G. V. Mallo et al., *Curr Biol* 12, 1209 (Jul. 23, 2002).
43. D. O'Rourke, D. Baban, M. Demidova, R. Mott, J. Hodgkin, *Genome Res* 16, 1005 (August, 2006).
44. K. Yook, J. Hodgkin, *Genetics* (Dec. 6, 2006).

What is claimed is:

1. A method of identifying an antifungal compound, the method comprising:
    (a) providing a co-culture comprising a *C. elegans*, *E. coli*, and a fungal pathogen comprising a mutant gene;
    (b) determining whether the fungal pathogen infects the *C. elegans*, wherein a lack of infection identifies the protein encoded by the wild type correlate of the mutant gene as a virulence factor;
    (c) exposing a wild type fungal pathogen that expresses the virulence factor to a test compound; and
    (d) determining whether the test compound inhibits expression of the virulence factor, wherein a decrease in the expression of the virulence factor indicates that the test compound is an antifungal compound.

2. The method of claim 1, wherein the fungal pathogen is *S. cerevisiae*.

3. The method of claim 1, wherein the fungal pathogen comprises a mutation in a gene that is expressed in the fungal pathogen but not in a mammal.

* * * * *